US00PP34247P2

(12) United States Plant Patent
Harrison

(10) Patent No.: US PP34,247 P2
(45) Date of Patent: May 17, 2022

(54) ***BOUGAINVILLEA* PLANT NAMED 'MONHARR'**

(50) Latin Name: *Bougainvillea communis*
Varietal Denomination: Monharr

(71) Applicant: Monrovia Nursery Company Inc., Azusa, CA (US)

(72) Inventor: Tracy Harrison, Whigham, GA (US)

(73) Assignee: Monrovia Nursery Company Inc., Azusa, CA (US)

( * ) Notice: Subject to any disclaimer, the term of this patent is extended or adjusted under 35 U.S.C. 154(b) by 0 days.

(21) Appl. No.: 17/369,013

(22) Filed: Jul. 7, 2021

(51) Int. Cl.
*A01H 5/02* (2018.01)
*A01H 6/00* (2018.01)

(52) U.S. Cl.
USPC ..... Plt./256

(58) Field of Classification Search
USPC ..... Plt./256, 263.1, 226
CPC ... A01H 5/02; A01H 5/00; A01H 5/12; A01H 5/06; A01H 6/00; A01H 6/30
See application file for complete search history.

(56) References Cited

PUBLICATIONS

Nova *Bougainvillea* Burgundy Queen in hanging basket 2001, retrieved on Sep. 22, 2021, retrieved from the Internet at https://nova.co.at/marsNova/en/instance/picture/Bougainvillea-Burgundy-Queen-in-hanging-basket.xhtml?oid=44105, 2 pp. (Year: 2001).*
Monrovia Grow Beautifully 2021 Monrovia Introduces New, Distinctive Varieties for 2022, retrieved on Sep. 22, 2021, retrieved from the Internet at https://agfstorage.blob.core.windows.net/misc/FD_com/2021/07/12/monrovia_pdf.pdf, 3 pp. (Year: 2021).*

* cited by examiner

*Primary Examiner* — June Hwu
(74) *Attorney, Agent, or Firm* — Cassandra Bright

(57) ABSTRACT

A new and distinct *Bougainvillea* plant named 'Monharr' is disclosed, characterized by dark burgundy-colored new growth, burgundy-colored bracts, an upright growth habit, and abundant flowers. The new variety is a *Bougainvillea*, typically produced as an ornamental plant.

2 Drawing Sheets

Latin name of the genus and species: *Bougainvillea communis.*

Variety denomination: 'Monharr'.

BACKGROUND OF THE INVENTION

The new cultivar is the product of chance discovery. The new variety originated as naturally occurring whole plant mutation of the variety *Bougainvillea communis* 'Barbara Karst', unpatented. The inventor discovered the variety in a commercial planting of the parent variety at a commercial nursery in Cairo, Ga., in the Summer of 2013.

After identifying the interesting mutation, first propagation was performed by terminal vegetative cuttings at a commercial greenhouse during 2013, in Cairo, Ga. The new variety was successfully rooted in 2016.

Through subsequent propagation by vegetative cuttings, multiple generations have been reproduced, which have shown that the unique features of this cultivar are stable and reproduced true to type.

SUMMARY OF THE INVENTION

The cultivar 'Monharr' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Monharr'.

These characteristics in combination distinguish 'Monharr' as a new and distinct *Bougainvillea* cultivar:

1. Dark burgundy-red new growth in each flush.
2. Burgundy-colored bracts.
3. Abundant flowering.
4. Upright plant habit. PARENT COMPARISON Plants of the new cultivar 'Monharr' are similar to the parent 'Barbara Karst', in most horticultural characteristics. However, characteristics of the new cultivar differ in the following:

1. The new variety has dark burgundy-colored new growth, while the parent does not.

COMMERCIAL COMPARISON

Plants of 'Monharr' are similar in some horticultural characteristics to the variety *Bougainvillea* 'Purple Queen', unpatented. The new variety, however, differs in the following:

1. The new growth of 'Monharr' has a more dramatic color than that of 'Purple Queen'.

Plants of 'Monharr' are similar in some horticultural characteristics to the variety *Bougainvillea* 'San Diego Red', unpatented. The new variety, however, differs in the following:

1. The new variety has burgundy-colored bracts, while 'San Diego Red' does not.
2. The new variety produces more flowers than 'San Diego Red'.

BRIEF DESCRIPTION OF THE PHOTOGRAPHS

Figure 1:
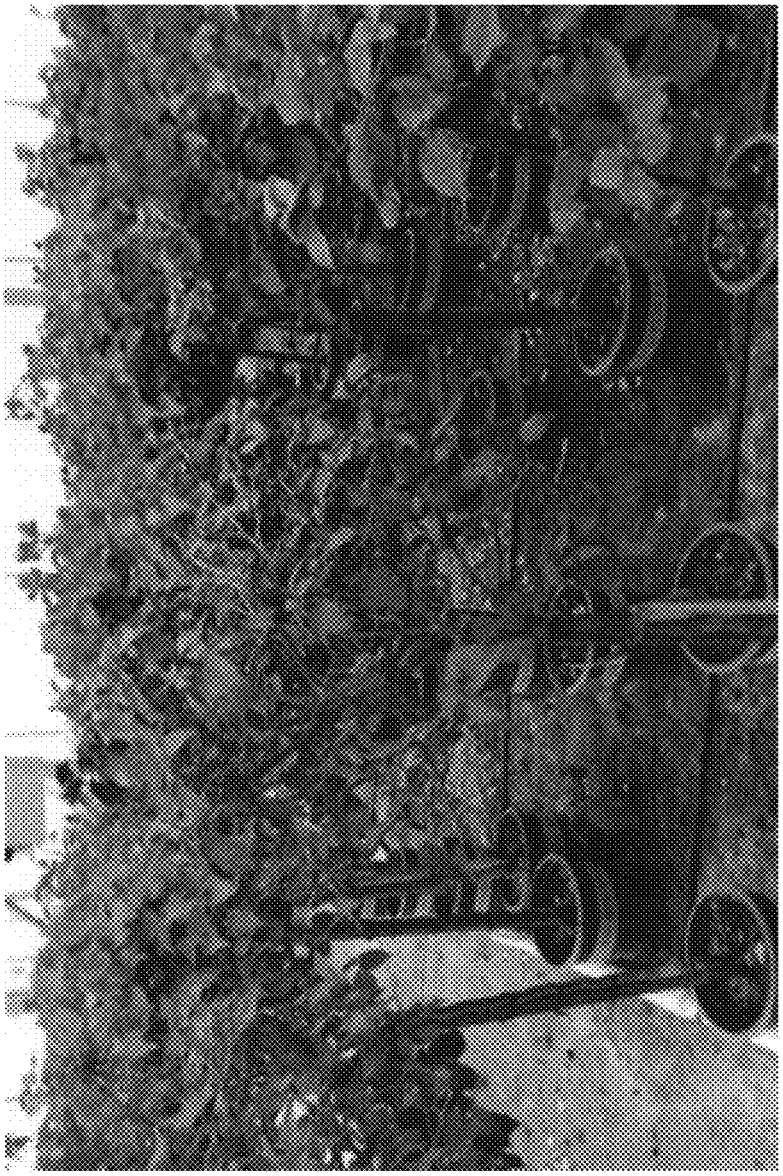

The accompanying photograph in FIG. 1 illustrates in full color a typical plant of 'Monharr' grown at a commercial nursery in Cairo, Ga., next to the parent variety, 'Barbara Karst'. The new variety is in the center of the photograph, with the clearly burgundy foliage compared to the green foliage of the plants surrounding the new variety. These plants are approximately 16 months old, shown in 3-gallon pots.

Figure 2:
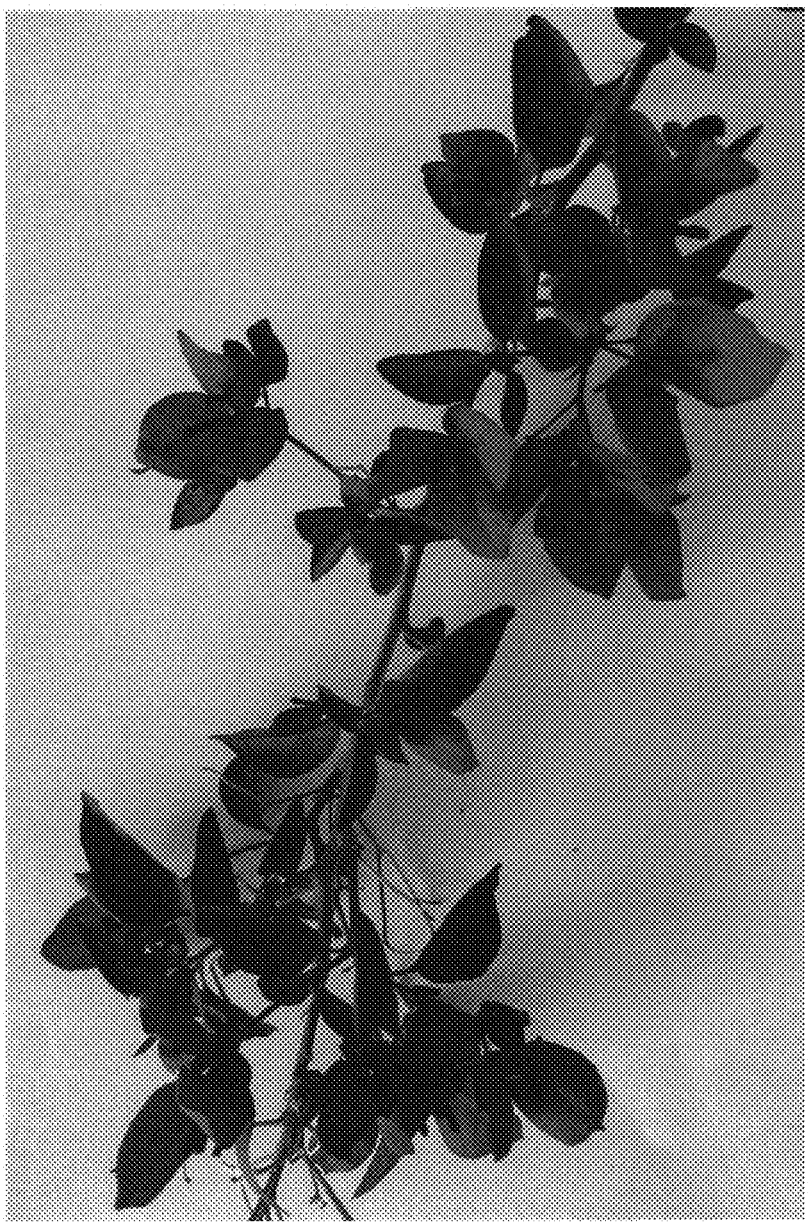

FIG. 2 illustrates a closer view of the foliage and flowering bracts.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe a 'Monharr' plant. This plant was grown in a greenhouse in a commercial 3-gallon pot, in Visalia, Calif. The plant described is approximately 1.8 months old and consists of 1 rooted cutting in 1 pot. No artificial light, photoperiodic treatments were given to the plants. Measurements and numerical values represent averages of typical plant types.

Botanical classification: *Bougainvillea communis* 'Monharr'.

PROPAGATION

Time to initiate roots: 14-21 days at approximately 25° C.
Root description: Roots are fine, fibrous and well branched.
Time to produce a rooted plant: Approximately 6 to 12 weeks.
Root color: Near RHS Grey-Brown 199D and Greyed-Yellow 161D.

PLANT

Growth habit: This plant is an upright tender perennial, suitable for indoor ornamental use, or outdoor garden use in warm climates.
Pot size of plant described: 5 gallon.
Height: 120 cm.
Plant spread: 60 cm.
Main stem color: Near RHS Grey 201B, striated Greyed-Green 197A.
Main stem texture: Striated.
Branching characteristics: Average 3 breaks from a pinch.
Length of primary lateral branches: 30 to 60 cm.
Quantity of primary lateral branches: 3 per plant.
Characteristics of primary lateral branches:
- *Diameter*.—Approximately 4 to 9 mm.
- *Color*.—Near RHS Greyed-Purple 183B.
- *Texture*.—Rough, thickly striated.

Internode length: 1.5 to 2.0 cm.

FOLIAGE

Leaf:
- *Arrangement*.—Alternate, simple.
- *Quantity*.—Approximately 12 to 20 per branch on a 2-year-old plant.
- *Average length*.—4 cm to 4.5 cm.
- *Average width*.—2.9 cm to 3.7 cm.
- *Shape of blade*.—Obovate.
- *Apex*.—Acute.
- *Base*.—Obtuse.
- *Margin*.—Entire.
- *Texture of top surface*.—Smooth.
- *Texture of bottom surface*.—Smooth.
- *Appearance of top surface*.—Matte.
- *Appearance of bottom surface*.—Matte.

Color:
- *Young foliage upper side*.—Near RHS Greyed-Purple 183A.
- *Young foliage under side*.—Near RHS Greyed-Purple 183A.
- *Mature foliage upper side*.—Near RHS Green 137B.
- *Mature foliage under side*.—Near RHS Green 143C.

Venation:
- *Type*.—Pinnate.
- *Venation color, upper side*.—RHS Yellow-Green 144C.
- *Venation color, under side*.—RHS Yellow-Green 145C.

Petiole:
- *Length*.—Average 1.1 cm to 2.8 cm.
- *Diameter*.—2 to 3 mm.
- *Color*.—Upper surface: Near RHS Yellow-Green 145A. Lower surface: Near RHS Yellow-Green 145A, lightly flushed Greyed-Purple 186B.
- *Texture*.—Slightly rough.

Other characteristics:
Thorns: Thorn density is moderate. One thorn occurs above a node. Thorn is pointed outward; Young thorns are more flexible and less sharp. Old thorns are very sharp, strong and woody.
- *Average thorn length*.—Mature thorn approximately 2.5 cm.
- *Average thorn width at base*.—3 mm.
- *Shape*.—Needlelike.
- *Thorn curvature*.—None, straight.
- *Thorn coloration*.—RHS Greyed-Orange 165D, base Greyed-Orange 166A.

FLOWER

Normal flowering period: Continuously from early Spring through Fall in temperate climates.
Inflorescence:
- *Form*.—Axillary, densely clustered cyme.
- *Width of entire inflorescence*.—Average 20.0 cm.
- *Height of entire inflorescence*.—Average 20.0 cm.
- *Quantity of individual flowers per branch*.—Average range of 20 to 30 on a 2-year-old plant. 3 to 7 bract clusters per cyme.
- *Flower longevity on plant*.—Approximately 10 days.
- *Quantity of inflorescence per plant*.—Average 30 to 50.
- *Quantity of bract clusters*.—Very dense. Average 30 to 50 on a 2-year-old plant.
- *Persistent or self-cleaning*.—Self-cleaning.

Bud:
- *Shape*.—Tubular.
- *Length*.—1.5 cm.
- *Diameter*.—3 mm.
- *Color*.—Near RHS Red-Purple 59B.

Individual true flower:
- *Form/type*.—Single, tubular flowers growing from the base of a single bract. The flowers have no petals or sepals. The individual true "flower" is small, and each cluster of three flowers is surrounded by three bracts. Sometimes the cluster consists of less flowers, but the number of bracts is nearly always 3.

*Diameter.*—7 mm.

*Length.*—2.2 cm.

*Days lasting on plant.*—Approximately one week.

Petals: 5 petals fully fused into a long tubular symmetrical flower, outwardly flared at apex.

*Tip.*—Acute.

*Base.*—Fused.

*Margin.*—Unfused upper-section crenate.

*Color.*—Upper Section, Immature: RHS Red-Purple N66C. Under Section, Immature: RHS Red-Purple 61A with thin stripes 61D. Tube Immature Outside Surface: RHS Red-Purple 61A. Tube Immature Inside Surface: RHS Greyed-Purple 187D. Upper Section, Mature: RHS Red-Purple 69A heavily stripes 61A. Tube Mature Outside Surface: RHS Red-Purple 61A. Tube Mature Inside Surface: RHS Red-Purple 61A Bracts:

*Days lasting on plant.*—Approximately 12, self-cleaning.

*Type.*—Single.

*Shape.*—Ovate.

*Length.*—3.5 cm.

*Width.*—2.5 cm.

*Tip.*—Acute.

*Base.*—Truncate.

*Margin.*—Entire.

*Aspect.*—Moderately undulating and reflexed back.

*Color.*—Under Side of Immature Bract: RHS Red-Purple 59A. Upper Side of Immature Bract: RHS Red-Purple 59B. Under Side of Mature Bract: RHS Red-Purple 61A. Upper Side of Mature Bract: RHS Red-Purple 61A.

Sepals: No sepals observed.

Peduncles:

*Length.*—Average 2.5 cm.

*Diameter.*—2 mm.

*Angle.*—Approximately 45° to the lateral branch.

*Strength.*—Strong.

*Texture.*—Smooth.

*Color.*—Near RHS Greyed-Purple 187B.

Pedicels:

*Arrangement.*—Individual flowers in whorls of 3, together on pedicels. Each individual flower sessile, implanted in a colorful bract.

*Length.*—2 cm.

*Diameter.*—2 mm.

*Angle.*—Average angle of 45°.

*Strength.*—Moderately strong.

*Color.*—Near RHS Greyed-Purple 187B.

Fragrance: None.

REPRODUCTIVE ORGANS

Malformed, irregular, less than 1 to 2 mm.

OTHER CHARACTERISTICS

Seeds and fruits: Seed production not observed.

Disease/pest resistance: Neither resistance nor susceptibility to diseases or pests has been observed in this variety.

Drought tolerance: No drought tolerance. Leaves and bracts will drop off the plant immediately under dry conditions.

What is claimed is:

1. A new and distinct cultivar of *Bougainvillea* plant named 'Monharr' as herein illustrated and described.

* * * * *